United States Patent [19]

Wallshein

[11] E Re. 29,686

[45] Reissued *Jul. 4, 1978

[54] ORTHODONTIC ELASTIC BAND WITH VARYING OUTER PERIPHERY

[76] Inventor: Melvin Wallshein, 8645 Bay Pkwy., Brooklyn, N.Y. 11214

[ * ] Notice: The portion of the term of this patent subsequent to Apr. 29, 1992, has been disclaimed.

[21] Appl. No.: 789,458

[22] Filed: Apr. 21, 1977

Related U.S. Patent Documents

Reissue of:

[64] Patent No.: 3,961,421
Issued: Jun. 8, 1976
Appl. No.: 566,752
Filed: Apr. 10, 1975

U.S. Applications:

[63] Continuation-in-part of Ser. No. 310,574, Nov. 29, 1972, Pat. No. 3,879,850.

[51] Int. Cl.[2] ..... A61C 7/00
[52] U.S. Cl. ..... 32/14 A
[58] Field of Search ..... 132/89, 91, 92, 93; 32/58, 59, 14 A

[56] References Cited

U.S. PATENT DOCUMENTS

| | | | |
|---|---|---|---|
| 3,174,787 | 3/1965 | Kolman | 32/14 A |
| 3,593,421 | 7/1971 | Brader | 32/14 A |

*Primary Examiner*—Robert Peshock
*Attorney, Agent, or Firm*—Flynn & Frishauf

[57] ABSTRACT

An orthodontic elastic band appliance, for use with an orthodonitic bracket which defines a channel, comprises a generally elongated elastic member having protuberances along the length thereof, the protuberances being in the form of, for example, spaced or adjacent nodules. Alternatively, the band may be in the form of an elongated strand with spaced, generally radially directed, cut-out portions along the length thereof so as to provide an orthodontic elastic band with alternately arranged larger and smaller dimension portions. The band may also comprise two strands twisted together and heat sealed together so as to form an overall elastic band of irregular outer circumference, or a single elastic strand having spaced twists set therein. The external dimensions of the elastic band, including the largest cross-sectional portions thereof, may be of any desired value, larger or smaller than the opening of the channel of the orthodontic bracket. The irregularly shaped outer surface of the orthodontic band facilitates tying knots in same and in weaving same between teeth in a stretched condition so as to apply appropriate corrective orthodontic forces.

77 Claims, 12 Drawing Figures

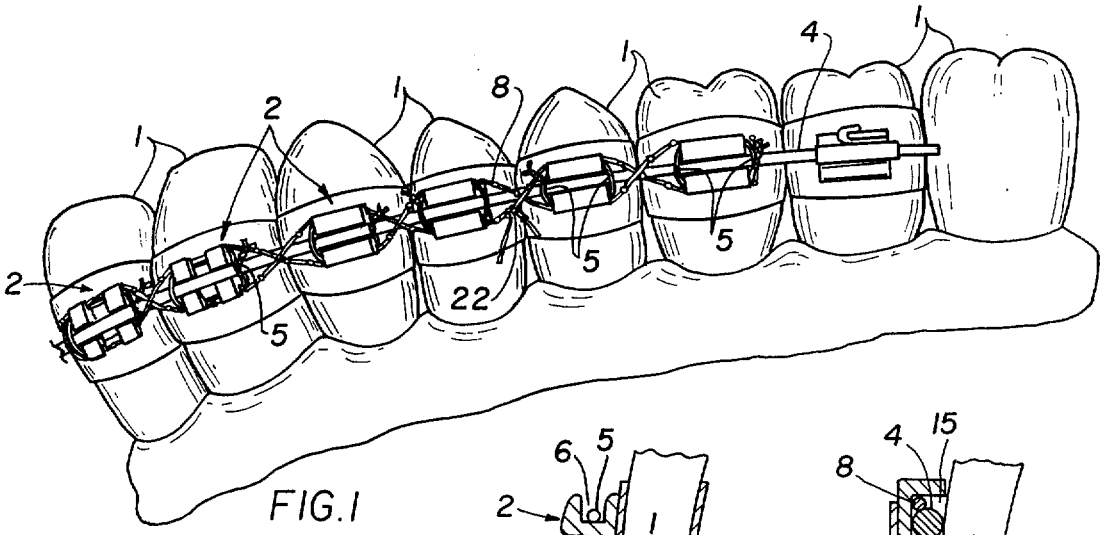
FIG.1
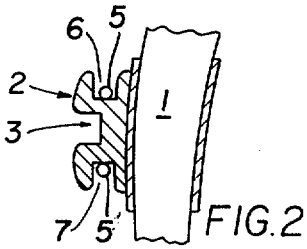
FIG.2
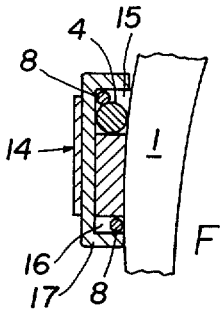
FIG.10
FIG.6
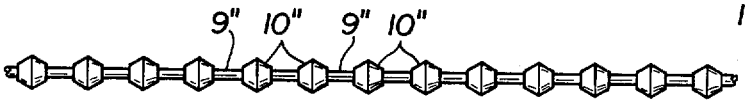
FIG.8a
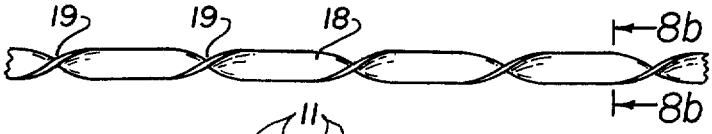
FIG.8b
FIG.5
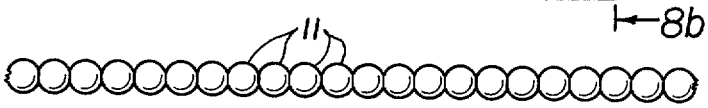
FIG.9
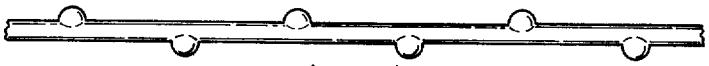
FIG.4
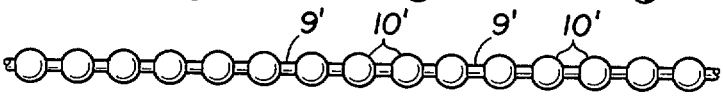
FIG.3
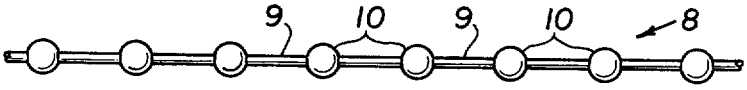
FIG.7a
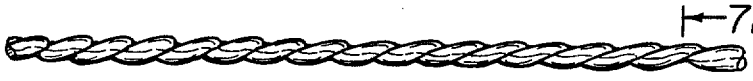
FIG.7b
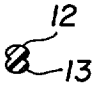

ORTHODONTIC ELASTIC BAND WITH VARYING OUTER PERIPHERY

Matter enclosed in heavy brackets [ ] appears in the original patent but forms no part of this reissue specification; matter printed in italics indicates the additions made by reissue.

CROSS-REFERENCE TO RELATED APPLICATION

This is a continuation-in-part of U.S. application Ser. No. 310,574, filed Nov. 29, 1972, now U.S. Pat. No. 3,879,850, issued Apr. 29, 1975.

BACKGROUND OF THE INVENTION

The present invention relates to orthodontic band appliances, and particularly to an elastic orthodontic band particularly suitable for use with orthodontic brackets which are mounted on teeth for transmitting forces to the brackets when the elastic band is deformed. In particular, the present invention is directed to an elastic band which facilitates use in a patient's mouth, especially when the band must extend in a stretched condition between several brackets, and to facilitate tying a knot at the end thereof after the band has been properly stretched between the patient's teeth.

The orthodontic band commonly used for the above purpose consists merely of an elongated, smooth surface, elastic band. However, when used in the mouth, such elastic bands are slippery and difficult to handle. Moreover, when being "woven" among a plurality of orthodontic brackets with the elastic band in a stretched condition, it is difficult to maintain the band in a uniformly stretched condition during the complete mounting operation. For example, if tension is released from the conventional smooth surfaced orthodontic band during mounting thereof, the band will relax and it will be necessary for the operator to then go back and restretch the band to insure that proper forces are applied. Moreover, after the band has been mounted between brackets in its appropriate stretched condition, it is necessary for the operator to tie the ends thereof in a knot so as to retain the band in its stretched condition. However, great difficulty is encountered in tying such a knot due to the fact that the band is slippery in the environment of the mouth and is therefore difficult to handle. Generally a second person is required in the knot tying operation to prevent releasing of tension in the conventional elastic band during the tying operation.

Accordingly, it is an object of the present invention to provide an orthodontic elastic band which overcomes the above-mentioned difficulties which arise when using the prior art bands.

SUMMARY OF THE INVENTION

In accordance with the present invention, an elongated elastic orthodontic band has alternately arranged larger and smaller dimension portions relative to a substantially straight axial line passing through the elongated band, the dimensions being taken in the same direction and in a common plane containing the straight axial line. In a preferred embodiment, the elastic band has alternately arranged larger and smaller diameter portions provided by protuberances, either spaced or adjacent each other. In another preferred embodiment, a desired variable or undulating surface configuration in the axial direction is obtained by twisting and heat sealing together two elongated elastic bands, or twisting and heat setting a single elastic band. The larger portions of the elastic band of the present invention may be smaller in overall size than the opening of the orthodontic bracket through which the band is to be passed. It has been found that even when the larger portions of the band are smaller than the bracket openings, secure retention of the band is still achieved since the band is generally angularly oriented relative to the bracket when it passes out of the bracket opening. Thus, the larger portions, in cooperation with the smaller portions of the band, retain the elastic band in a stretched condition between orthodontic brackets even when the operator releases tension on the free end of the orthodontic elastic band. Moreover, the arrangement of the present invention facilitates tying of a knot after the band has been installed in a patient's mouth, substantially eliminating the inadvertent relaxing of the band and resultant release of tension, and eliminating the necessity of having a second person cooperate with the operator in tying the knot.

The orthodontic band of the present invention is preferably wholly made from elastic material with the larger portions integral with the smaller portions. Alternatively, the band may be made of several elastic pieces bonded or otherwise sealed together. Still further, the protuberances on the elastic band may comprise in elastic material connected to a strand of elastic material in any conventional manner. The particular shape of the protuberances on the elastic band, or the particular shape of the irregular or undulating outer surface thereof, is not a major controlling factor. Various shapes may be used.

BRIEF DESCRIPTION OF THE DRAWINGS

FIG. 1 is a front elevational view of a plurality of teeth having brackets mounted thereon, with an arch wire extending between said teeth, and with an elastic orthodontic band according to the present invention mounted thereon;

FIG. 2 is a section view of the bracket shown in FIG. 1, in an enlarged state;

FIG. 3 is a front elevational view of one embodiment of an elastic band in accordance with the present invention;

FIG. 4 is a front elevational view of another embodiment of an elastic band in accordance with the present invention;

FIG. 5 is a front elevational view of still another embodiment of an elastic band in accordance with the present invention;

FIG. 6 is a front elevational view of a further embodiment of an elastic band in accordance with the present invention;

FIG. 7a is a front elevational view of a still further embodiment of an elastic band in accordance with the present invention;

FIG. 7b is a sectional view of the arrangement of FIG. 7a taken along line 7b–7b in FIG. 7a;

FIG. 8a is a front elevational view of a still further embodiment of an elastic band in accordance with the present invention;

FIG. 8b is a sectional view of the arrangement of FIG. 8a taken along line 8b–8b in FIG. 8a;

FIG. 9 is a front elevational view of another embodiment of an elastic band in accordance with the present invention; and FIG. 10 is a sectional view of another type of bracket with which the invention is useful.

DETAILED DESCRIPTION OF ILLUSTRATED EMBODIMENTS

Referring to FIG. 1, a plurality of teeth 1 have respective brackets 2 mounted thereon in a conventional manner. FIGS. 2 and 10 illustrate end sectional views of typical brackets 2,14, respectively mounted on a tooth 1. The brackets 2,14 are conventional, the bracket of FIG. 2 being illustrated in the drawings of copending parent application Ser. No. 310,574, the contents of which are incorporated herein by reference.

The brackets 2 have openings 3 (see FIG. 2) for receiving an arch wire 4 therein (see FIG. 1). The arch wire 4 is retained in the openings 3 of the brackets 2 by means of wires 5 which pass around the arch wires 4 and through the openings 6,7 of the brackets 2. The ends of the wires 5 are twisted as shown in FIG. 1 to retain the arch wire in the bracket openings 3 in a conventional manner. Elastic rings can be used to retain arch wire 4. As shown in FIG. 10 another conventional bracket 14 defines an opening or channel 15 with the tooth 1, and further defines an opening or channel 16 with the tooth 1 and locking pin 17 thereof. Either opening 15,16 may receive the elastic band of the present invention therein.

Referring to FIGS. 1 and 2, after the arch wire 4 is mounted in openings 3 of the brackets 2, an orthodontic elastic band 8 is "woven" through the openings 6,7 of the brackets 2 in a stretched condition so as to provide orthodontic forces to the brackets 2 which are secured to the teeth 1, to tend to move the teeth 1 in a desired direction, depending upon the application of the elastic forces created by the arch wire 4 and elastic band 8. In order to facilitate securing the elongated elastic band 8, the elastic band 8 of the present invention is provided with a variable outer periphery in the axial direction of the elongated band, the variable periphery being at least in a plane passing through the longitudinal axis of the elongated band. This peripheral configuration of the elastic band permits the operator to release tension on the end of the band without the band relaxing over a substantial length thereof which had been previously woven or mounted to the brackets 2. This is because enlarged or protruding portions of the elastic band of the present invention will engage the end of an opening 6 or 7 of the bracket 2 when tension in the band is released, thereby preventing substantial portions of the already mounted band from totally relaxing as has been a difficulty with the prior art.

FIG. 3 illustrates a first embodiment of the invention wherein the elastic band 8 comprises strand portions 9 having enlarged nodules or protuberances 10 spaced along the length thereof. The nodules 10 may be formed integrally with the strand 9 or may be added to the strand 9 later. Preferably, the nodules 10 are integral with the strand 9 and both are made from an elastomeric material, such as rubber or plastic. However, the nodules 10 need not be made from an elastic material. Still further, the nodules 10 need not be generally spherical in shape as shown in FIG. 3. The exact shape of the nodules 10 is not critical and if desired, they may take the shape as illustrated by nodules 10" in FIG. 6. The nodules may take any convenient shape, as long as the variable outer peripheral configuration of the strand 8 results so that the protruding portions of the strand 8 may engage the ends of the openings 6,7 of a bracket 2 to prevent relaxing of the strand.

In accordance with the present inventive concept, it is not necessary that the nodules 10 be of larger dimension than the openings of the channels 6,7 in the bracket 2. This is because, as shown in FIG. 1, the elastic band is generally engaged with the brackets such that the band 8 leaves the opening of a channel of the bracket at an angle such that the band tends to press against the lower or base portion of the channels 6,7 of the bracket 2. Therefore, the undulating or irregular outer periperal surface of the elastic band 8 will tend to grip the edge of the opening of the bracket channels and be prevented by this action from relaxing from its stretched condition. Moreover, as shown in FIGS. 1 and 2, the bracket channels 6,7 generally have a wire 5, or an arch wire retaining elastic ring already mounted therein before the elastic band 8 is applied to the brackets. See, for example, FIGS. 1 and 2. Therefore, since the already present wire 5 or the already present elastic arch wire retaining ring takes up a portion of the channels 6,7 this will enhance the engagement or wedging of the band 8 of the present invention with the brackets to prevent relaxing thereof when tension forces are released from the ends, even when the size of the nodules is substantially less than the cross-sectional dimension of the channels 6,7.

Still further, the provision of the nodules 10 facilitates tying of the knot 11 at the free ends of the elastic band 8. When the first loop of the knot is made, the nodules 10 will interengage with each other to prevent the first loop of the knot from loosening while the operator is making the second securing loop of the knot. Heretofore, using prior art smooth surfaced elastic bands, it has been necessary for the operator to use external means to retain the first loop of the knot to prevent loosening of the elastic band and resultant loss of corrective forces. This is no longer necessary with the elastic band of the present invention.

FIG. 4 illustrates the modified embodiment of the elastic band of the present invention wherein the nodules 10' are more closely spaced than in the embodiment of FIG. 3. Similar resultant effects are obtained when using the embodiment of FIG. 4 as with the embodiment of FIG. 3.

FIG. 5 illustrates a further example of the present invention wherein the elastic band is formed of a plurality of adjacent nodules 11. The nodules 11 may be integrally formed with each other, for example by a molding technique, or may be individual nodules adhered together, for example by a heat treatment. The nodules 11 are made of an elastic material so that the resultant elastic band may be stretched between brackets 2 to provide tooth moving forces.

A modified embodiment, similar to that of FIG. 5, may have a saw-tooth outer peripheral configuration, and would provide similar resultant effects to the previously discussed embodiments.

FIG. 7 illustrates a further embodiment of the invention wherein the desired peripheral shape is achieved by twisting two strands 12 and 13 (see FIG. 7b) and heat treating the twisted strands so as to seal them together as illustrated in FIG. 7b and in order to provide an appropriate "set" to the material so that it retains its spiral configuration as shown in FIG. 7a. Experiments have shown that this embodiment is not quite as satisfactory as the embodiments discussed above, but by virtue of the undulating surface in any given plane which passes through the longitudinal axis of the elastic band, retention effects with the channels 6,7 (FIG. 2) and 15,16 (FIG. 10) of the brackets and when tying knots are still achieved to such a degree that the band is useful in accordance with the present invention. Again, the elastic band of FIGS. 7a and 7b is fabricated of an elastomeric material which can be stretched to provide tooth moving forces.

FIG. 8 shows another embodiment comprised of an elastic band 18 of rectangular cross-section with a plurality of spaced twists 19 formed therein. The twisted band is heat set to retain its twisted shape. The twisted areas 19 may comprise any number of twists sufficient to define the smaller dimension portions of the resulting band. The band 18 may also have a square or any other convenient starting shape which would result in smaller dimension portions 19 when twisted.

While in the above description embodiments of the invention are described wherein the widest portion of the elastic band, in a direction perpendicular to the longitudinal axis of the band, are smaller than the width of the channels 6,7 in the bracket 2, it should be clear that the nodules or other widest portions of the elastic band may be larger than the width of the channels 6,7 defined by the bracket 2. When the widest portions are larger than the channels defined by the bracket, it is advantageous to use spaced protuberances or nodules which are interconnected by smaller strand portions, such as portions 9 or 9' of FIGS. 3 and 4, respectively, the strand portions 9,9' being of small enough dimension to easily fit within the channel 6,7 of the bracket. Also even, if the widest portions are larger than the channels 6,7, when they are elastomeric, as preferred, they reduce in size when stretched, thereby fitting in channels 6,7 or channels 15,16.

While the invention has been described above with respect to specific shapes, it should be clear that these shapes are given merely by way of example and are not limiting of the inventive concept. Moreover, while the embodiments of FIGS. 3–6 are shown to be symmetrical in a plane perpencidular to the longitudinal axis of the band, it should be clear that non-symmetrical arrangements, such as shown in FIG. 9, for example, may be provided. That is, the protuberances may be semicircular in a plane perpendicular to the longitudinal axis of the band, or any other desired off-set or irregular shape to provide undulating or varying peripheral shapes in the longitudinal direction of the elastic band.

It should be clear that various modifications and alterations may be made to the embodiments shown within the scope of the presnt inventive concept as set forth in the claims.

I claim:

1. An orthodontic elastic band for use with orthodontic bracket means mountable on teeth, each bracket means at least partially defining an opening of predetermined cross-sectional dimension adapted to receive at least a portion of an orthodontic elastic band therein, at least one of said bracket openings having at least one engaging and retaining surface adjacent thereto, said elastic band comprising an elongated elastic member having, distributed over a substantial length thereof, alternately arranged portions of larger and smaller dimensions relative to a substantially straight and substantially central axial line passing through the elongated band when it is in a straight condition, said dimensions being taken in the same direction in a common plane containing said substantially straight axial line, said larger dimensions portions [being] *comprising abutment portions which are* dimensioned such that when said elastic band is stretched along its length and is at least partially engaged in an opening defined by at least one orthodontic bracket means, *at least one of* said larger dimension [portion] *abutment portions* abuttingly engages at least a portion of said at least one engaging and retaining surface to substantially prevent the stretched elastic band from relaxing, and when knotting the ends thereof, at least two of said larger dimension portions engaging each other to substantially prevent the stretched elastic band from relaxing.

2. An orthodontic elastic band according to claim 1 wherein said smaller dimension portions comprises *elastic* strands of predetermined length, and said larger dimension portions comprise respective *elastic* nodules interposed between adjacent strands.

3. An orthodontic elastic band according to claim 2 wherein said nodules are generally spherical in shape.

4. An orthodontic elastic band according to claim 3 wherein said strands each have a length larger than the diameter of said spherical nodules.

5. An orthodontic elastic band according to claim 3 wherein said strands have a length equal to or shorter than the diameter of said spherical nodules.

6. An orthodontic elastic band according to claim 1 wherein said smaller dimension portions comprise elastic portions of given length and said larger dimension portions comprise *elastic* protuberances extending in a direction perpendicular to said substantially straight axial line and extending over at least a portion of the periphery of said band in a plane perpendicular to said substantially straight axial line.

7. An orthodontic elastic band according to claim 1 comprising a plurality of *elastic* nodules adjacent each other and directly connected to each other, the plane of interconnection of said nodules comprising said smaller dimension portions.

8. An orthodontic elastic band according to claim 7 wherein said nodules are substantially spherical and the central portions of said nodules comprise said larger dimension portions.

9. An orthodontic elastic band according to claim 1 having an undulating outer surface in the axial direction thereof.

10. An orthodontic elastic band according to claim 1 having a [non-pymmetrical] *substantially symmetrical* outer periphery, relative to said substantially straight axial line, in any plane perpendicular to said straight axial line.

11. An orthodontic elastic band according to claim 1 having a non-symmetrical outer periphery, relative to said substantially *straight* axial line, in any plane perpendicular to said straight axial line.

12. An orthodontic elastic band according to claim 1 wherein said band comprises an elongated strand having a plurality of spaced twisted portions therein, said twisted portions defining said smaller dimension portions.

13. An orthodontic elastic band according to claim 12 wherein said strand is generally rectangular between said twisted portions.

14. An orthodontic elastic band according to claim 1 wherein said alternately arranged portions of larger and smaller dimensions are over substantially the whole length thereof.

15. An orthodontic elastic band according to claim 1 comprising an elongated elastic strand having a plurality of spaced *elastic* protuberances extending therefrom in a direction perpendicular to said substantially straight axial line, said protuberances extending over at least a portion of the periphery of said band in a plane perpendicular to said substantially straight axial line.

16. An orthodontic elastic appliance, comprising:

an elongated elastic band; and at least one bracket means mountable on teeth, each bracket means at least partially defining an opening of predetermined cross-sectional dimension adapted to receive at least a portion of said elastic band therein, at least one of said bracket openings having at least one engaging and retaining surface adjacent thereto, said elastic band comprising an elongated elastic member having, distributed over a substantial length thereof, alternately arranged portions of larger and smaller dimensions relative to a substantially straight and substantially central axial line passing through the elongated band when it is in a straight condition, said dimensions being taken in the same direction in a common plane containing said substantially straight axial line, said larger dimension portions [being] *comprising abutment portions which are* dimensioned such that when said elastic band is stretched along its length and is at least partially engaged in said bracket opening, [said larger dimension portion] *at least one of said larger dimension abutment portions* abuttingly engages at least a portion of said at least one engaging and retaining surface to substantially prevent the stretched elastic band from relaxing.

17. An orthodontic appliance according to claim 16 wherein said larger dimension portions are dimensioned such that when knotting the ends of the elastic band, at least two of said larger dimension portions engage each other to substantially prevent the stretched elastic band from relaxing.

18. An orthodontic appliance according to claim 16 wherein said at least one bracket means comprises a band mounted to a tooth, and a bracket fixedly mounted to said band with a predetermined orientation relative to said band.

19. An orthodontic elastic appliance according to claim 18 wherein said bracket opening is defined completely by said bracket.

20. An orthodontic elastic appliance according to claim 18 wherein said bracket opening is delimited partially by said bracket and partially by a surface of a tooth on which said bracket is mounted.

21. An orthodontic appliance according to claim 18 wherein said bracket opening is delimited partially by said bracket and partially by a surface of said band which is mounted to said tooth.

22. An orthodontic elastic appliance according to claim 16 wherein said smaller dimension portions comprise *elastic* strands of predetermined length, and said larger dimension portions comprise respective *elastic* nodules interposed between adjacent strands.

23. An orthodontic elastic appliance according to claim 22 wherein said nodules are generally spherical in shape.

24. An orthodontic elastic appliance according to claim 23 wherein said strands each have a length larger than the diameter of said spherical nodules.

25. An orthodontic elastic appliance according to claim 23 wherein said strands have a length equal to or shorter than the diameter of said spherical nodules.

26. An orthodontic elastic appliance according to claim 16 wherein said smaller dimension portions comprise elastic portions of given length and said larger dimension portions comprise *elastic* protuberances extending in a direction perpendicular to said substantially straight axial line and extending over at least a portion of the periphery of said band in a plane perpendicular to said substantially straight axial line.

27. An orthodontic elastic appliance according to claim 16 comprising a plurality of *all-elastic* nodules adjacent each other and directly connected to each other, the plane of interconnection of said nodules comprising said smaller dimension portions.

28. An orthodontic elastic appliance according to claim 27 wherein said nodules are substantially spherical and the central portions of said nodules comprise said larger dimension portions.

29. An orthodontic elastic appliance according to claim 16 having an undulating outer surface in the axial direction thereof.

30. An orthodontic elastic appliance according to claim 16 having a substantially symmetrical outer periphery relative to said substantially straight axial line, in substantially any plane perpendicular to said straight axial line.

31. An orthodontic elastic appliance according to claim 16 having a non-symmetrical outer periphery relative to said substantially straight axial line, in any plane perpendicular to said straight axial line.

32. An orthodontic elastic appliance according to claim 16 wherein said band comprises an elongated strand having a plurality of spaced twisted portions therein, said twisted portions defining said smaller dimension portions.

33. An orthodontic elastic appliance according to claim 32 wherein said strand is generally rectangular between said twisted portions.

34. An orthodontic elastic appliance according to claim 16 wherein said alternately arranged portions of larger and smaller dimensions are over substantially the whole length thereof.

35. An orthodontic elastic band comprising an elongated elastic member having, distributed over a substantial length thereof, alternately arranged portions of larger and smaller dimensions relative to a substantially straight and substantially central axial line passing through the elongated band when it is in a straight condition, said dimensions being taken in the same direction in a common plane containing said substantially straight axial line, said larger and smaller dimension portions being dimensioned such that the distance between two adjacent larger dimension portions is no greater than about twice the length of said larger dimension portions in the direction of said substantially straight axial line, [and such that] *said smaller dimension portions comprising elastic strands of predetermined length, and said larger dimension portions comprising respective elastic nodules interposed between adjacent strands, whereby* when the elastic band is stretched along its length and portions thereof are knotted, at least two of said larger dimension portions engage each other to substantially prevent the stretched elastic band from relaxing.

36. An orthodontic elastic band according to claim 35 wherein said larger dimension portions are substantially identical with each other and wherein said smaller dimension portions are substantially identical with each other.

[37. An orthodontic elastic band according to claim 35 wherein said smaller dimension portions comprise strands of predetermined length, and said larger dimension portions comprise respective nodules interposed between adjacent strands.]

38. An orthodontic elastic band according to claim 37 wherein said nodules are generally spherical in shape.

39. An orthodontic elastic band according to claim 38 wherein said strands each have a length larger than the diameter of said spherical nodules.

40. An orthodontic elastic band according to claim 38 wherein said strands have a length equal to or shorter than the diameter of said spherical nodules.

[41. An orthodontic elastic band according to claim 35 wherein said smaller dimension portions comprise elastic portions of given length and said larger dimension portions comprise protuberances extending in a direction perpendicular to said substantially straight axial line and extending over at least a portion of the periphery of said band in a plane perpendicular to said substantially straight axial line.]

42. An orthodontic elastic band according to claim 35 comprising a plurality of nodules adjacent each other and directly connected to each other, the plane of interconnection of said nodules comprising said smaller dimension portions.

43. An orthodontic elastic band according to claim 42 wherein said nodules are substantially spherical and the central portions of said nodules comprise said larger dimension portions.

44. An orthodontic elastic band according to claim 35 having an undulating outer surface in the axial direction thereof.

45. An orthodontic elastic band according to claim 35 wherein said alternately arranged portions of larger and smaller dimensions are over substantially the whole length thereof.

46. An orthodontic elastic band according to claim 35 wherein the distance between two adjacent larger dimension portions is no greater than the length of said larger dimension portions.

47. An orthodontic elastic band according to claim 1 wherein the distance between two adjacent larger dimension portions is no greater than about twice the length of said larger dimension portions in the direction of said substantially straight axial line.

48. An orthodontic elastic appliance according to claim 16 wherein the distance between two adjacent larger dimension portions is no greater than about twice the length of said larger dimension portions in the direction of said substantially straight axial line.

49. An orthodontic elastic band according to claim 1 wherein said larger dimension portions have a maximum dimension no greater than the smallest cross-sectional dimension of said bracket opening.

50. An orthodontic elastic appliance according to claim 16 wherein said larger dimension portions have a maximum dimension no greater than the smallest cross-sectional dimension of said bracket opening.

*51. A method of using an orthodontic elastic band with at least one orthodontic element, the elements each having at least one engaging and retaining surface, and said elastic band comprising an elongated elastic member having, distributed over a substantial length thereof, alternately arranged portions of larger and smaller dimensions relative to a substantially straight and substantially central axial line passing through the elongated band when it is in a straight condition, said larger dimension portions comprising abutment portions for abuttingly engaging at least a portion of said at least one engaging and retaining surface of the elements, the method comprising:*

*engaging said elastic band in a stretched condition with at least one of said elements; and*

*causing at least one abutment portion of said elastic band to abut against said engaging and retaining surface of said at least one element such that said elastic band remains in its stretched condition.*

*52. A method according to claim 51 wherein said orthodontic elements each have means at least partially defining an opening of predetermined cross-sectional dimension for receiving at least a portion of the orthodontic elastic band therein, said at least one engaging and retaining surface being adjacent said opening; comprising passing said elastic band through an opening of at least one of said orthodontic elements in said stretched condition.*

*53. A method according to claim 51 wherein said at least one orthodontic element comprises an orthodontic bracket means which at least partially defines an opening of predetermined cross-sectional dimension for receiving at least a portion of an orthodontic elastic band therein, said at least one engaging and retaining surface being adjacent said opening, comprising passing said elastic band in said stretched condition through the bracket opening of at least one bracket and causing said at least one abutment portion of said elastic band to abut against said engaging and retaining surface of said at least one bracket.*

*54. A method according to claim 53 comprising passing said elastic band through the bracket openings of a plurality of bracket means with said elastic band being stretched between two adjacent bracket means; relaxing said elastic band after passing same through a bracket opening whereby at least one abutment portion of said elastic band abuts against said engaging and retaining surface of at least one of said bracket means so that said elastic band remains in its stretched condition between said two adjacent bracket means; and passing said elastic band through a further bracket opening of a bracket means in a stretched condition.*

*55. A method according to claim 51 comprising tying at least one end of said elastic band, said larger dimension abutment portions of said elastic band engaging said band to substantially prevent the stretched elastic band from relaxing.*

*56. A method according to claim 55 comprising tying two ends of said stretched elastic band together, said larger dimension abutment portions engaging each other to substantially prevent the stretched elastic band from relaxing.*

*57. An orthodontic elastic band for use with at least one orthodontic element, each element having at least one engaging and retaining surface,*

*said elastic band comprising an elongated elastic member having, distributed over a substantial length thereof, alternately arranged portions of larger and smaller dimensions relative to a substantially straight and substantially central axial line passing through the elongated band when it is in a straight condition, said dimensions being taken in the same direction in a common plane containing said substantially straight axial line, said larger dimension portions comprising*

*abutment portions which are dimensioned such that when said elastic band is stretched along its length and is at least partially engaged with an orthodontic element said larger dimension abutment portions abuttingly engages at least a portion of said at least one engaging and retaining surface to substantially prevent the stretched elastic band from relaxing, and when knotting the ends thereof, at least two of said larger dimension portions engaging each other to substantially prevent the stretched elastic band from relaxing.*

*58. An orthodontic elastic band according to claim 57 wherein said smaller dimension portions comprise elastic strands of predetermined length, and said larger dimension portions comprise respective elastic nodules interposed between adjacent strands.*

*59. An orthodontic elastic band according to claim 58 wherein said nodules are generally spherical in shape.*

*60. An orthodontic elastic band according to claim 59 wherein said strands each have a length larger than the diameter of said spherical nodules.*

*61. An orthodontic elastic band according to claim 59 wherein said strands have a length equal to or shorter than the diameter of said spherical nodules.*

*62. An orthodontic elastic band according to claim 57 comprising a plurality of elastic nodules adjacent each other and directly connected to each other, the plane of interconnection of said nodules comprising said smaller dimension portions.*

*63. An orthodontic elastic band according to claim 62 wherein said nodules are substantially spherical and the central portions of said nodules comprise said larger dimension portions.*

*64. An orthodontic elastic band according to claim 57 having an undulating outer surface in the axial direction thereof.*

*65. An orthodontic elastic band according to claim 57 comprising an elongated elastic strand having a plurality of spaced elastic protuberance extending therefrom in a direction perpendicular to said substantially straight axial line, said protuberances extending over at least a portion of the periphery of said band in a plane perpendicular to said substantially straight axial line.*

*66. An orthodontic appliance, comprising:*

*an elongated elastic band; and*

*at least one orthodontic element adapted to be engaged by said elastic band, said at least one element having at least one engaging and retaining surface;*

*said elastic band comprising an elongated elastic member having, distributed over a substantial length thereof, alternately arranged portions of larger and smaller dimensions relative to a substantially straight and substantially central axial line passing through the elongated band when it is in a straight condition, said dimensions being taken in the same direction in a common plane containing said substantially straight axial line, said larger dimension portions comprising abutment portions which are dimensioned such that when said elastic band is stretched along its length and is at least partially engaged with an orthodontic element, at least one of said larger dimension abutment portions abuttingly engages at least a portion of said at least one engaging and retaining surface to substantially prevent the stretched elastic band from relaxing.*

*67. An orthodontic appliance according to claim 66 wherein said larger dimension portions are dimensioned such that when knotting the ends of the elastic band, at least two of said larger dimension portions engage each other to substantially prevent the stretched elastic band from relaxing.*

*68. An orthodontic appliance according to claim 66 wherein said at least one orthodontic element comprises a band mounted to a tooth, and an element fixedly mounted to said band with a predetermined orientation relative to said band, said element defining an opening for receiving at least a portion of said elastic band therein, said opening being adjacent said at least one engaging and retaining surface.*

*69. An orthodontic appliance according to claim 68 wherein said opening is defined completely by said orthodontic element.*

*70. An orthodontic appliance according to claim 68 wherein said opening is delimited partially by said element and partially by a surface of said band which is mounted to said tooth.*

*71. An orthodontic appliance according to claim 66 wherein said orthodontic element is mountable on a tooth, said element defining an opening for receiving at least a portion of said elastic band therein, said opening being adjacent said at least one engaging and retaining surface.*

*72. An orthodontic appliance according to claim 71 wherein said opening is delimited partially by said element and partially by a surface of a tooth on which said element is mounted.*

*73. An orthodontic appliance according to claim 66 wherein said smaller dimension portions comprise elastic strands of predetermined length, and said larger dimension portions comprise respective elastic nodules interposed between adjacent strands.*

*74. An orthodontic appliance according to claim 73 wherein said nodules are generally spherical in shape.*

*75. An orthodontic appliance according to claim 74 wherein said strands each have a length larger than the diameter of said spherical nodules.*

*76. An orthodontic appliance according to claim 74 wherein said strands have a length equal to or shorter than the diameter of said spherical nodules.*

*77. An orthodontic appliance according to claim 66 comprising a plurality of all-elastic nodules adjacent each other and directly connected to each other, the plane of interconnection of said nodules comprising said smaller dimension portions.*

*78. An orthodontic appliance according to claim 77 wherein said nodules are substantially spherical and the central portions of said nodules comprise said larger dimension portions.*

*79. An orthodontic appliance according to claim 66 having an undulating outer surface in the axial direction thereof.*

* * * * *